Figure 1:
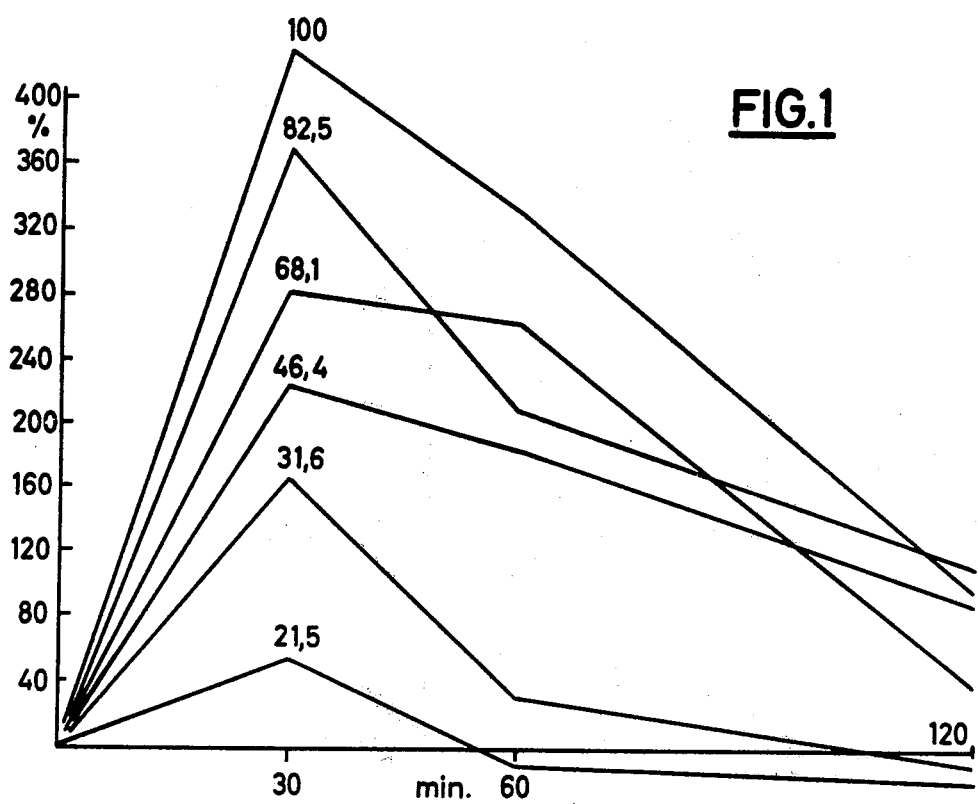

United States Patent [19]

Amann et al.

[11] 3,965,119

[45] June 22, 1976

[54] CARBAMATES AND THEIR USE AS PHARMACEUTICALS

[75] Inventors: August Amann, Ludwigshafen; Gerhard Bolz, Frankenthal; Walter-Wielant Wiersdorff, Ludwigshafen; Hubert Giertz, Limburgerhof; Klaus Wilsmann, Ludwigshafen, all of Germany

[73] Assignee: BASF Aktiengesellschaft, Ludwigshafen (Rhine), Germany

[22] Filed: Sept. 13, 1974

[21] Appl. No.: 505,756

[30] Foreign Application Priority Data
Sept. 14, 1973 Germany............................ 2346305

[52] U.S. Cl. ................. 260/343.3 R; 260/247.2 B; 260/293.58; 260/326.34; 260/343.6; 424/248; 424/267; 424/274; 424/279
[51] Int. Cl.$^2$................ C07D 307/77; C07D 307/93
[58] Field of Search.................. 260/343.3, 247.2 B, 260/293.58, 326.34

Primary Examiner—James A. Patten
Attorney, Agent, or Firm—Johnston, Keil, Thompson & Shurtleff

[57] ABSTRACT

Carbamates derived from polycyclic γ-hydroxylactones and their production. The compounds may be used as pharmaceuticals by virtue of their analgesic properties.

4 Claims, 5 Drawing Figures

CARBAMATES AND THEIR USE AS PHARMACEUTICALS

The invention relates to new carbamates derived from substituted γ-hydroxylactones, to their production and to their use as pharmaceuticals.

The new compounds may be represented by the general formula (I):

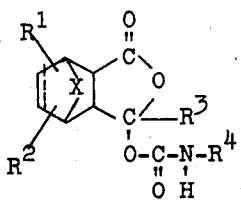

(I)

In this formula the dotted line represents a double bond which may be hydrogenated:

X is a carbon bridge having a total of from one to 10 carbon atoms which may be linear or branched, saturated or unsaturated and may be part of a cycloaliphatic ring;

$R^1$ to $R^4$ may each be hydrogen or linear or branched alkyl of one to eight carbon atoms and moreover the alkyl $R^4$ may be unsaturated or saturated or $R^4$ may be a cycloaliphatic, bicycloaliphatic or polycycloaliphatic radical or four to eight carbon atoms in the ring or an aromatic radical which may bear substituents.

Examples of the said radicals are: linear or branched saturated carbon bridges for X are for example: methylene, ethylene-1,2, propylene-1,3, propylene-1,2, butylene-1,4, 1,2-dimethylethylene-1,2, 1,1,3-trimethylethylene-1,2 and 1,1-dimethylmethylene.

Examples of linear or branched unsaturated carbon bridges for X are: vinylene, vinylidene, 2,2-dimethylvinylidene, 2-ethyl-2-methylvinylidene and 2,2-diethylvinylidene.

Examples of carbon bridges for X which are part of a saturated or unsaturated cycloaliphatic ring of three to six carbon atoms are: cyclopropylene-1,2, cyclobutylene-1,2 and cyclobuten-(3)-ylene-1,2.

Preferred compounds are those in which X is —(CH$_2$-)$_n$— where $n$ is an integer of from 1 to 4 and of these ethylene and methylene are particularly preferred.

Examples of radicals for $R^1$ to $R^3$, which may be identical or different, are (in addition to hydrogen): methyl, ethyl, propyl, isopropyl, butyl, isobutyl, sec.-butyl, tert.butyl, amyl, hexyl, heptyl, 2-ethylhexyl and octyl.

In the preferred compounds $R^1$ to $R^3$ are hydrogen or alkyl of up to four carbon atoms.

$R^4$ may have the meanings and preferred meanings given above for $R^1$ to $R^3$. Moreover the alkyls for $R^4$ may be unsaturated. Examples of radicals having double bonds or triple bonds are: vinyl, ally, methallyl, but-1-en-3-yl, but-2-en-3-yl, propargyl, but-1-yn-3-yl, pent-1-yn-3-yl, pent-2-yn-3-yl, 4-methylpent-1-yn-4-yl and 3-ethylpent-1-yn-3-yl.

The alkyls for $R^4$ may bear substituents, for example halogen atoms such as chlorine, bromine or iodine, alkoxy of one to four carbon atoms such as methoxy, ethoxy, propoxy, butoxy or isopropoxy, thioalkyl of one to four carbon atoms such as methylthio, ethylthio, propylthio, isopropylthio or butylthio, dialkylamino of one to four carbon atoms in the alkyl which may bear substituents, or cyclic amino groups of five to seven members in the ring such as dimethylamino, diethylamino, dipropylamino, diisopropylamino, di-n-butylamino, methylethylamino, pyrrolidino, piperidino, morpholino, hexamethylenimino or aromatic radicals and particularly phenyl.

Examples of cycloaliphatic, bicycloaliphatic or polycycloaliphatic radicals for $R^4$ are cyclobutyl, cyclopentyl, 2-methylcyclopentyl, cyclohexyl, cyclooctyl, bicyclo-(2,2,2)-octyl, norbornyl and radicals containing the norbornene or camphor ring system.

Examples of aromatic radicals for $R^4$ are phenyl and phenyl having one or more radicals as substituents, particularly suitable substituents being halogen atoms such as chlorine, bromine or iodine, alkyl and preferably methyl or ethyl, or tert.-amino groups such as dimethylamino or diethylamino.

Examples of substituted phenyl radicals are o-chlorophenyl, m-chlorophenyl, p-chlorophenyl, 3,4-dichlorophenyl, o-toluyl, p-toluyl, 4-ethylphenyl and 4-dimethylaminophenyl.

In the preferred compounds $R^4$ is hydrogen or linear or branched, saturated or unsaturated alkyl of one to four carbon atoms which may bear chloro, alkoxy, amino or phenyl as substituents. Examples are methyl, ethyl, propyl, isopropyl, butyl, isobutyl, sec.-butyl, tert.-butyl, vinyl, allyl, β-chloroethyl, methoxymethyl, methoxyethyl, β-ethoxyethyl, propoxymethyl, β-methylthioethyl, β-dimethylamino, β-diethylamino, β-piperidinoethyl, benzyl or β-phenylethyl.

The following compounds are examples of compounds according to the invention:

4-oxa-5-(N-methoxymethylcyrbamoyloxy)-tricyclo[5,2,2,0$^{2,6}$]-undecan-3-one, 4-oxa-5-(N-methylcarbamoyloxy)-tricyclo[5,2,2,0$^{2,6}$]-undecan-3-one, 4-oxa-5-(N-ethylcarbamoyloxy)-tricyclo[5,2,2,0$^{2,6}$]undec-8-en-3-one, 4-oxa-5-(carbamoyloxy)-tricyclo[5,2,2,0$^{2,6}$]undec-8-en-3-one, 4-oxa-5-(carbamoyloxy)-tricyclo[5,2,1,0$^{2,6}$]decan-3-one, 4-oxa-5-(N-n-propylcarbamoyloxy)-tricyclo[5,2,1,0$^{2,6}$]decan-3-one, 4-oxa-5-(N-β-chloroethylcarbamoyloxy)-tricyclo[5,2,1,0$^{2,6}$]decan-3-one, 4-oxa-5-(N-β-(N',-N'-dimethylaminoethyl)-carbamoyloxy)-tricyclo[5,2,1,0$^{2,6}$]dec-8-en-3-one, 4-oxa-5-ethyl-5-(N-methylcarbamoyloxy)-tricyclo[5,2,1,0$^{2,6}$]dec-8-en-3-one, 4-oxa-5-methyl-5-(N-ethylcarbamoyloxy)-tricyclo[5,2,1,0$^{2,6}$]dec-8-en-3-one, 4-oxa-5-(N-methoxymethylcarbamoyloxy)-tetracyclo[5,3,2,0$^{2,6}$0$^{8,10}$]-dodec-11-en-3-one, 4-oxa-5-(N-methylcarbamoyloxy)-tetracyclo[5,4,2,0$^{2,6}$0$^{8,11}$]trideca-9,12-dien-3-one.

Compounds of formula (I) according to the invention may be prepared by the reaction of a substituted γ-hydroxylactone of the general formula (II):

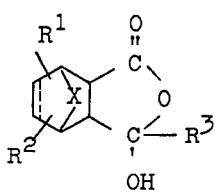

(II)

with an isocyanate of the general formula (III):

R⁴—N=C=O  (III)

or the hydrochloric acid adduct of the same, a carbamoyl chloride of the general formula (IV)

which is capable of liberating the isocyanate under the reaction conditions in the presence of a base. R¹ to R⁴ and X in the formulae (II), (III) and (IV) have the meanings given above.

When an unsaturated compound of formula (II) is used as starting material the double bond may be hydrogenated by a conventional method.

Another method of preparing the compounds of formula (I) according to the invention consists in the reaction of a 1,3-diene of the formula (V):

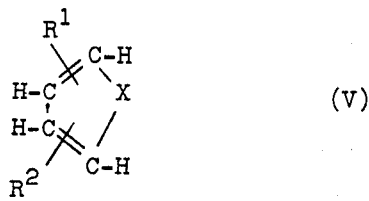

with a dienophile of the general formula (VI):

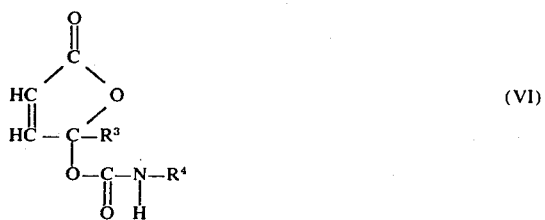

in which R¹ to R⁴ and X have the meanings given above and the double bond in the Diels-Alder product obtained may if desired then be hydrogenated.

The reaction of compounds of formula (II) with the isocyanates of formula (III) is conveniently carried out in an inert organic solvent, for example tetrahydrofuran, benzene, n-hexane, chloroform or methyl isobutyl ketone at room temperature or an elevated temperature, preferably at a temperature of from 15° to 120°C.

The presence of a catalyst for the purpose such as dibutyl tin diacetate, tin octanoate or triethylene diamine in an amount of from 0.1 to 10% based on the weight of the starting compound of the formula (II) may be advantageous. The reaction may also be carried out in suspension or in the absence of a solvent.

The reaction of a compound of the formula (II) with a carbamoyl chloride of the formula (IV) may be carried out conveniently in one of the abovementioned solvents and in the temperature range of from 15° to 120°C. It is convenient to add an acid-binding agent, a tertiary organic base, for example pyridine or triethylamine, of an alkali metal carbonate or hydroxide such as potassium hydroxide or an aqueous suspension of calcium oxide. These reactions may also be carried out in a two-phase heterogeneous system.

The Diels-Alder reaction of compounds of formula (IV) with compounds of the formula (VI) may be carried out in a conventional manner conveniently in an inert organic solvent or diluent at a temperature of from 15° to 220°C. It may also be carried out without a solvent. Examples of suitable solvents or diluents are benzene, toluene, chlorobenzene, chloroform, carbon tetrachloride, dioxane, an ether, ethyl acetate or acetone. Carrying out the process while using a pressure of up to 50 atmospheres may be advantageous.

Hydrogenation of the double bond in the ring system of formula (I) may be carried out without difficulty by a conventional method.

A convenient method consists in dissolving or suspending the appropriate unsaturated carbamate in a solvent which is inert under hydrogenation conditions and hydrogenating it in the presence of a catalyst. Lower alcohols, for example methanol, ethanol, a dialkyl ether or cyclic ether such as diethyl ether, tetrahydrofuran or dioxane or a cyclic hydrocarbon such as cyclohexane may be used as solvents. Platinum metal catalysts, if desired on carriers, such as Pd/CaCO₃, Pd/carbon, Pt/carbon, platinum dioxide, or cobalt or nickel, if desired on carriers such as SiO₂, may be used. The hydrogenation may be carried out at room temperature or at elevated temperature and at atmospheric pressure or in an autoclave at superatmospheric pressure depending on the activity of the catalyst. After the necessary amount of hydrogen has been absorbed the catalyst is removed and the hydrogenation product is purified in the usual way by recrystallization. Hydrogenation is carried out at a temperature of from 10° to 100°C. Hydrogen pressures of up to 200 atmospheres may be used.

The starting compounds of formula (V) and (VI) are for the most part known compounds and may be prepared by methods known from the literature.

Compounds of the formula (VI) — N-substituted carbamoyl-2,5-dihydrofuran-5-ones — may be prepared by a conventional method from 2-hydroxy-2,5-dihydrofuran-5-ones and the appropriate isocyanates for example as described in Liebigs Ann. Chem. 697 (1966), 42 to 61.

It is not necessary and in the case of reaction products which are difficult to crystallize not even advisable to isolate the N-substituted carbamoyloxy-2,5-dihydrofuran-5-one thus synthesized and then react it with the desired diene, but the reaction mixture obtained may be directly used in the following Diels-Alder reaction. In principle the reaction may also be carried out by reacting the appropriate 2-hydroxy-2,5-dihydrofuran-5-one with the diene component and the isocyanate, if desired in the presence of a catalyst, in a one-vessel reaction to form the end product of formula (I).

The starting compounds of formula (II) may be prepared by a Diels-Alder reaction of a compound of formula (V) with an appropriately substituted 2-hydroxy-2,5-dihydrofuran-5-one of the formula (VII) as dienophile:

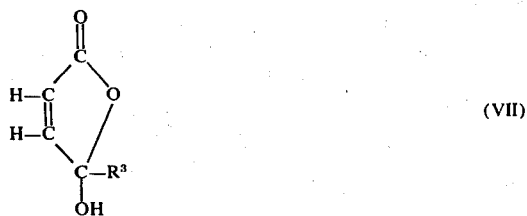
(VII)

R³ in the formula (VII) may have the meanings given above.

A convenient method is to place a solution of the dienophile (VII) in a vessel and to add the diene (V), if desired dissolved in a suitable solvent, at the rate at which it is consumed in the reaction. In some cases it is advisable to dissolve the diene and the dienophile in one another, if necessary using a solubilizer, and to effect the reaction for example in an autocalve. It may be convenient to protect the diene against polymerization by adding a stabilizer. The reaction is carried out at a temperature of from 20° to 110°C and particularly at 30° to 100°C. It is advantageous to use an organic solvent which is inert under the reaction conditions such as an aromatic hydrocarbon, such as benzene, toluene or xylene or an aliphatic or cycloaliphatic hydrocarbon such as n-hexane, petroleum ether, ligroin, cyclohexane, diethyl ether, dibutyl ether, dioxane, tetrahydrofuran, or also an alcohol or an ester.

Compounds of the formula (II) and their production form the subject matter of U.S. application Ser. No. 504,491 (9/9/74).

The compounds according to the invention have valuable pharmacological properties. They inhibit or stimulate certain functions of the central nervous system. A pronounced antinociceptive effect, for example in the hot plate test, the tail flick test, the writhing test or the Randall-Selitto test may be exhibited in the pharmacological investigation of test animals and the effective dosage is usually far below the range of toxic dosage.

The valuable pharmacological properties of the compounds according to the invention may be shown for example for 4-oxa-5-(N-methylcarbamoyloxy)-tricyclo[5,2,1,0²·⁶]dec-8-en-3-one. As may be seen from the following graphs this compound exhibits a pronounced antinociceptive effect on the test animal, on the mouse in the hot plate test, tail flick test and writhing test and on the rat in the Randall-Selitto test.

1. Hot plate test (FIG. 1)

The hot plate is kept at 57°C and reaction is appraised by the lifting off and simultaneous shaking of the hind legs. The period from being placed on the plate until the occurence of the said reaction is measured as the latency period. Observation is limited to 30 seconds.

FIG. 1 shows the latency prolongation in percent after different doses (21.5; 31.6; 46.4; 68.1; 82.5 and 100.0 mg/kg of body weight) in dependence on time (in minutes) after application. The percentage latency prolongation is plotted on the ordinates and the time after application (in minutes) on the abcissae.

2. Tail flick test (FIG. 2)

The source of heat used is an incandescent lamp (6 v, 5 w) in a concave reflector. The animals are placed singly in a measuring cage which is at a fixed distance from the heat source and the tail which has been passed out through a slot is irradiated. The period before there is a clear retraction of the tail is measured.

Figure 2:
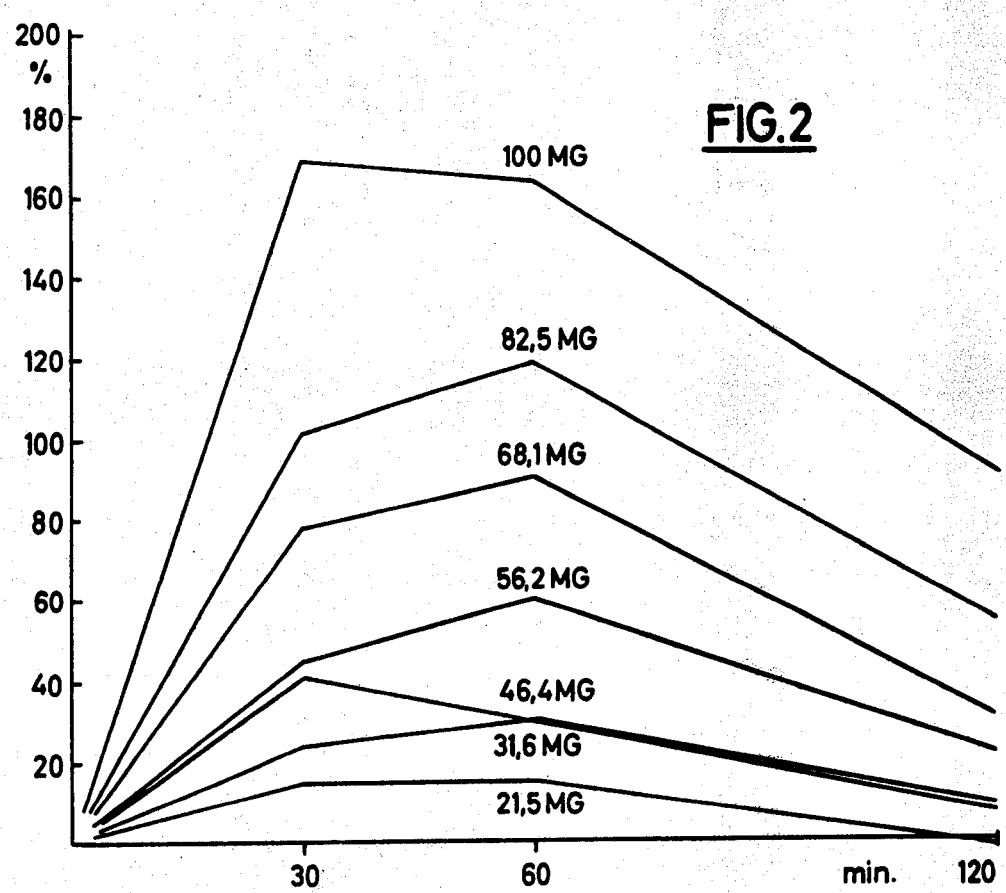

FIG. 2 shows the prolongation of latency in precent after different doses (21.5; 31.6; 46.4; 56.2; 68.1; 82.5 and 100 mg/kg of body weight) in dependence on time after application (in minutes). In FIG. 2 the percentage latency prolongation is plotted as ordinates and the time in minutes after application is plotted as abscissae.

3. Writhing test (FIG. 3)

Pain is initiated by p-benzoquinone in a 0.02% aqueous solution in a volume of 10 ml/kg of body weight i.p.. The measurable parameter is the latency (the period up to the first reaction) and the sum of the stretching reactions within 15 minutes of administration.

Figure 3:
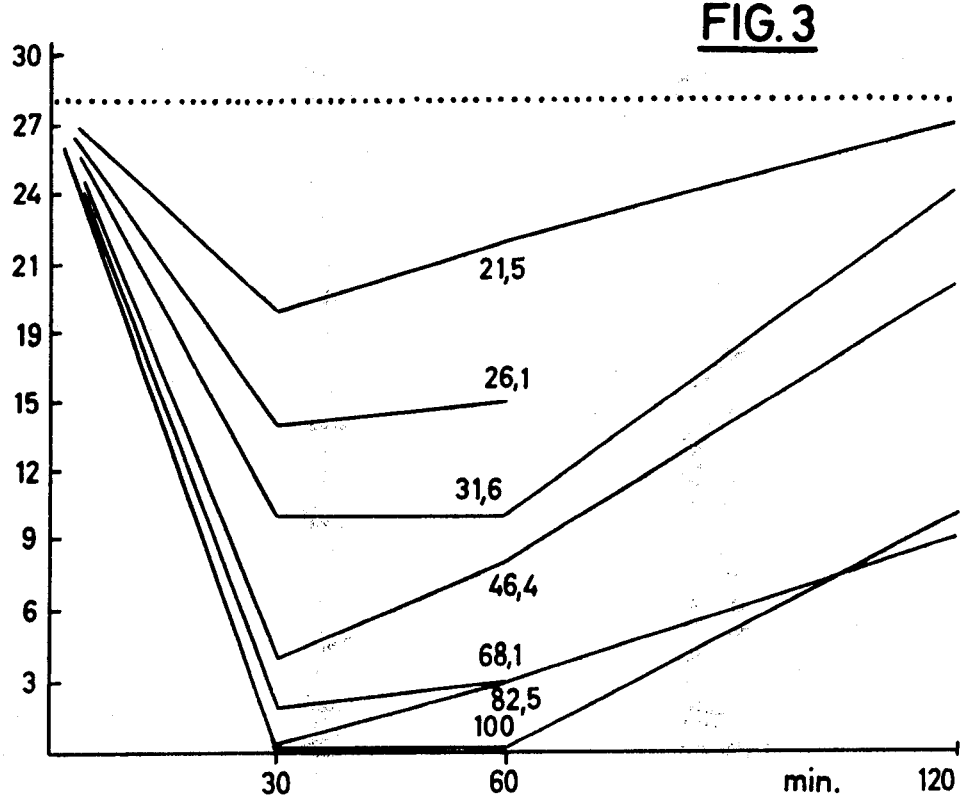

FIG. 3 shows the sum of the reactions within 15 minutes after different doses (00.0; 82.5; 68.1; 46.4; 31.6; 26.; and 21.5 mg/kg of body weight) in dependence on time (in minutes) after application. The sum of the reactions is plotted as ordinates in FIG. 3 and the time (in minutes) after application is plotted as abscissae.

4. Randall-Selitto test (FIG. 4)

The test equipment is the analgesia meter of Ugo Basile (Milan). To increase sensitivity to pain the rat receives 0.05 ml of a 1% aqueous carrageenin solution as a plantar s.c. injection in the left hind paw. The blank measurement is carried out 150 minutes after this injection. After the blank check the test substance is applied and measurement is taken 30, 60 and 120 minutes thereafter.

Figure 4:
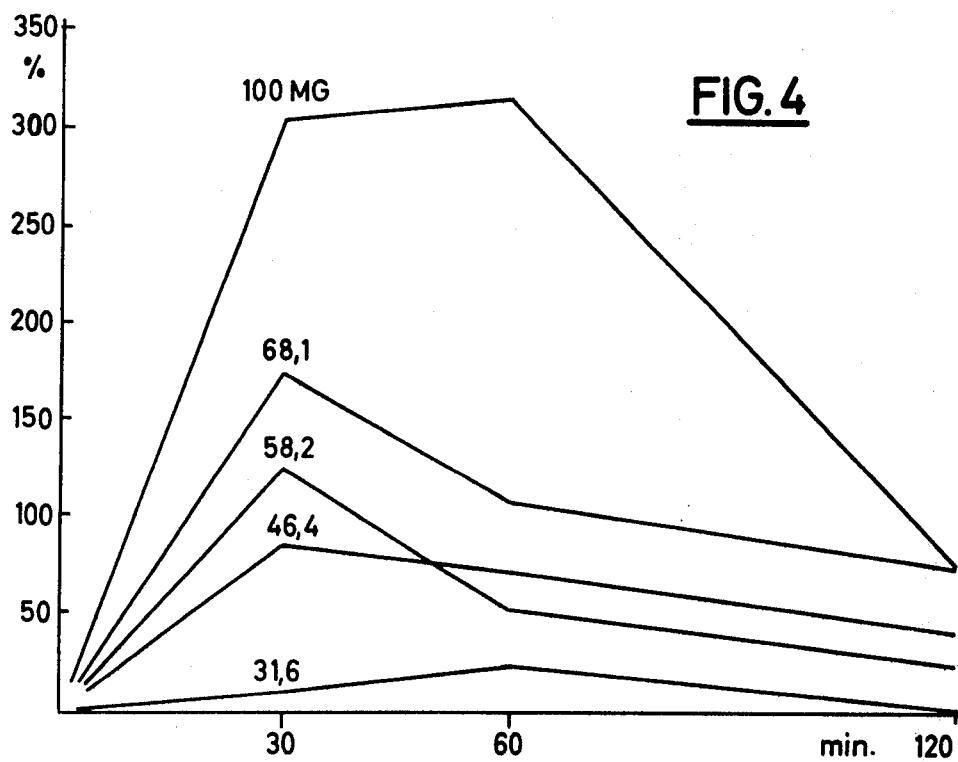

FIG. 4 shows the percentage increase in the paw load endured after different doses (31.6; 46.4; 58.2; 68.1 and 100.0 mg/kg of body weight) in dependence on time (in minutes) after application. The percentage increase in paw load is plotted as ordinates in FIG. 4 and the time after application is plotted as abscissae.

The substance tested has an effect in the analgesia test which is about 10 times as weak as morphine but without imparing respiration and circulation so that in spite of the weaker effect there is a greater therapeutic breadth. The therapeutic breadth is also greater as compared with dextropropoxyphene with a similar action.

In a pharmacological analysis of the effect on facilitated and unfacilitated reflex discharges of α-motoneurons carried out experimentally the effect mechanism of 4-oxa-5-(N-methylcarbamoyloxy)-tricyclo[5,2,1,0²·⁶]dec-8-en-3-one is about the same as that of morphine and differs clearly from DOLANTIN (Pethidine) and weaker analgesics such as phenacetin, aminophenazone and the like.

In tests on the effect on circulation and respiration in rabbits it is found that there is no appreciable effect on blood pressure and pulse frequency and no change in respiration volume for the said substance up to a dose of 215 mg/kg of body weight, whereas after morphine has been administered in doses of from 3.16 to 21.5 mg/kg of body weight the blood pressure and pulse frequency decline sharply depending on the dose and the respiration volume in this dose range falls to the point of failure of respiration and death of the animal.

Similar pharmacological effects may be shown in the case of other compounds according to the invention of which the following may be particularly mentioned: 4-oxa-5-(carbamoyloxy)-tricyclo[5,2,1,0$^{2,6}$]dec-8-en-3one, 4-oxa-5-(N-methylcarbamoyloxy)-tricyclo[5,2,2,0$^{2,6}$]undec-8-3n-3-one and 4-oxa-9-methyl-5-(N-methylcarbamoyl-oxy)-tricyclo[5,2,1,0$^{2,6}$]dec-8-en-3-one.

While having similar pharmacological effectiveness these compounds have in some cases less side effects so that the ratio of effects to side effects is more favorable.

Examples of further effective compounds are as follows:

4-oxa-5-(N-methylcarbamoyloxy)-tricyclo[5,2,1,0$^{2,6}$]decan-3-one,
4-oxa-1-methyl- 5-(N-methylcarbamoyloxy)-tricyclo[5,2,1,0$^{2,6}$]dec-8-en-3one,
4-oxa-5-(N-ethylcarbamoyloxy)-tricyclo[5,2,1,0$^{2,6}$]dec-8-en-3-one,
4-oxa-5-(N-propylcarbamoyloxy)-tricyclo[5,2,1,0$^{2,6}$]dec-8-en-3-one,
4-oxa-9-methyl-5-(N-ethylcarbamoyloxy)-tricyclo[5,2,1,0$^{2,6}$]dec-8-en-3-one, and
4-oxa-1-methyl-5-(N-methoxymethylcarbamoyloxy)-tricyclo-[5,2,1,0$^{2,6}$]dec-8-en-3-one.

Figure 5:
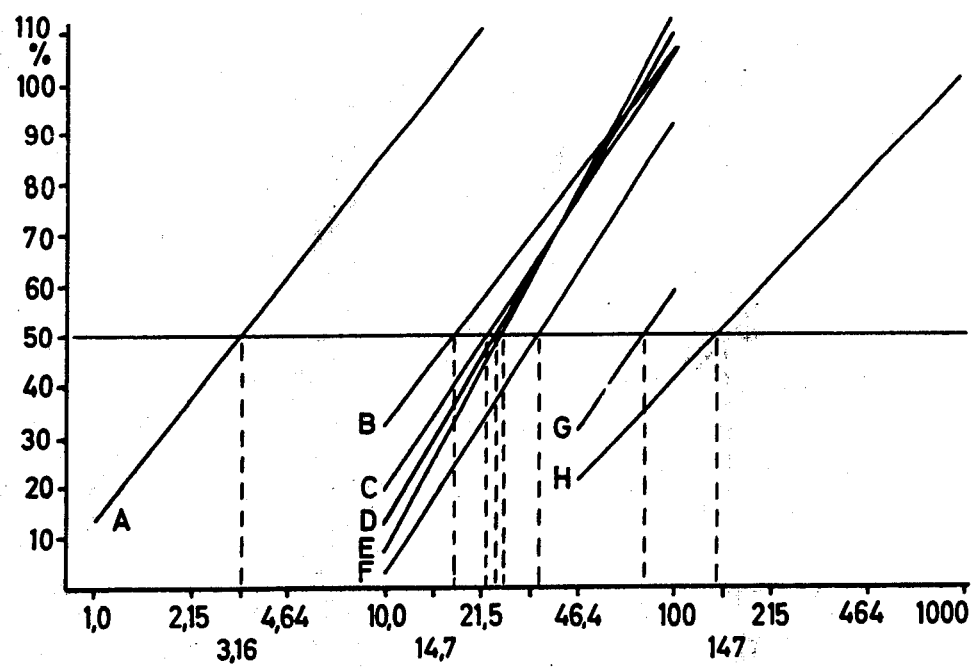

FIG 5 shows graphically dosage-effect relationship for the writhing test of different analgesics (morphine, curve A; tilidine, curve B; dextropropoxypitene, curve C; codeine, curve F; pentazocine, curve G; phenacetine, curve H) and of 4-oxa-5-(N-methylcarbamoyloxy)-tricyclo[5,2,1,0$^{2,6}$]dec-8-en-3-one, curve D and 4-oxa-5-carbamoyloxy)-tricyclo[5,2,1,0$^{2,6}$]dec-8-en-3-one, curve E.

The effect given as a percentage inhibition of the writhing reactions is plotted as ordinates and the dosds (mg/kg) are plotted logarithmically as abscissae. The point of intersection of the dotted vertical lines with the horizontal full line gives the ED$_{50}$, i.e. that does under which the number of writhing reactions is decreased by 50%.

The graph shows that the two substances according to the invention (curves D and E) have practically the same effect and should be classified among the medium strength analgesics tilidine, dextropropoxyphene and codeine.

Therapeutic agents which contain at least one compound of formula (I) as active ingredient may be prepared with conventional carriers or diluents and the conventionally used pharmaceutical auxiliaries in accordance with the type of application in a conventional way with a dosage suitable for use. These therapeutic agents may be used a analgesics for pain of medium and strong intensity. Individual doses of from 20 to 200 mg and preferably from 50 to 100 mg are suitable for the treatment of pain.

The preferred pharmaceutical preparations are in a form suitable for oral or parenteral administration. Such forms include in particular tablets, coated tablets, dragees, capsules, suppositories and preparations which contain the active ingredient, particularly a pharmacologically compatible salt, in an aqueous suspension, sterilized water, isotonic salt solution or other solution.

As a rule the preparations consist of the active ingredient to be used according to the invention with a carrier, or diluted with a carrier, or filled into or encapsulated by a carrier in the form of a capsule, bag, medicinal capsule or other container as a carrier substance which may serve as a medium, flavoring or diluent for the therapeutically active ingredient. This carrier may be a solid, semisolid or liquid substance.

Examples of carriers which may be used are: lactose, dextrose, sucrose, sorbitol, mannitol, starch, gum acacia, calcium phosphate, liquid paraffin, coconut butter, cocoa butter, alginates, tragacanth, gelatins, invert sugar syrup, methyl cellulose, polyoxyethylenesorbitan monolaurate, methylhydroxybenzoate and propylhydroxybenzoate. When preparing tablets a lubricant may be added to prevent the powdered components from sticking in the tablet mold or tablet press. Examples of suitable lubricants are talc, aluminum stearate, magnesium stearate and calcium stearate.

The following Examples will illustrate the production of the new compounds without the scope of the invention being limited to the specific Examples. The compounds are confirmed in their structure by analysis and spectral data.

EXAMPLE 1

4-oxa-5-(N-methylcarbamoyloxy)-tricyclo[5,2,1,0$^{2,6}$]-dec-8-en-3-one

A solution of 33.2 g of 4-oxa-5-hydroxytricyclo-[5,2,1,0$^{2,6}$]dec-8-en-3-one in 50 ml of tetrahydrofuran is heated with 11.4 g of methylisocyanate for 5 hours at 70°C and then cooled to 0°C. The crystals which have separated are suction filtered and recrystallized from methanol. The yield is 22.6 g of the melting point 160° to 163°C.

Elementary analysis (C$_{11}$H$_{13}$NO$_4$). Calculated: C, 58.8; H, 5.8; N, 6.3; 0, 28.7. Found: C, 58.9; H, 5.9; N, 6.2; 0, 28.3.

EXAMPLES 2 TO 12

Carbamates are prepared analogously to Example 1 from 4-oxa-5-hydroxytricyclo[5,2,1,0$^{2,6}$]dec-8-en-3-one and the appropriate isocyanate and are recrystallized from ethyl acetate or from a mixture of ethyl acetate and hexane. 4-oxa-5-(carbamoyl)-tricyclo[5,2,1,0$^{2,6}$]dec-8-en-3-ones in which the radical R$^4$ on the nitrogen has different meanings are contained in the following Table.

| Example | R$^4$ | Melting point (°C) |
|---------|-------|---------------------|
| 2 | C$_2$H$_5$ | 108 – 110 |
| 3 | i-C$_3$H$_7$ | 118 – 120 |
| 4 | n-C$_4$H$_9$ | 101 – 102 |
| 5 | CH$_2$—CH=CH$_2$ | 97 – 98 |
| 6 | CH$_2$—OCH$_3$ | 101 – 103 |
| 7 | (CH$_2$)$_2$—OC$_2$H$_5$ | 89 – 91 |
| 8 | 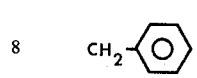 | 108 – 109 |
| 9 |  | 175 – 176 |

| Example | R⁴ | Melting point (°C) |
|---|---|---|
| 10 | (4-chlorophenyl) | 176 – 177 |
| 11 | (3-chlorophenyl) | 175 – 176 |
| 12 | (3,4-dichlorophenyl) | 189 – 190 |

EXAMPLES 13 TO 24

The following carbamates are prepared analogously to Example 1; melting points in °C are given in parenthesis: TC = tricyclo[5,2,1,0$^{2,6}$]; TC' = tetracyclo[5,3,2,0$^{2,6}$,0$^{8,10}$].

13. 4-oxa-5-methyl-(N-methylcarbamoyloxy)-TC-dec-8-en-3-one (99–101)
14. 4-oxa-5-methyl-5-(N-methoxymethylcarbamoyloxy)-TC-dec-8-en-3-one (96–100)
15. 4-oxa-5-(N-methylcarbamoyloxy)-TC-undec-8-en-3-one (145–147)
16. 4-oxa-5-(N-methoxymethylcarbamoyloxy)-TC-undec-8-en-3-one (121–122)
17. 4-oxa-5-(N-methylcarbamoyloxy)-TC'-dodec-1-en-3-one (172–175)
18. 4-oxa-10-isopropylidene-5-(N-methylcarbamoyloxy)-TC-dec-8-en-3-one (96–97)
19. 4-oxa-7-methyl-5-(N-methylcarbamoyloxy)-TC-dec-8-en-3-one (169–170)
20. 4-oxa-9-methyl-5-(N-methylcarbamoyloxy)-TC-dec-8-en-3-one (138–140)
21. 4-oxa-9-methyl-5-(N-ethylcarbamoyloxy)-TC-dec-8-en-3-one (111–114)
22. 4-oxa-9-methyl-5-(N-methoxymethylcarbamoyloxy)-TC-dec-8-en-3-one (99–103)
23. 4-oxa-1-methyl-5-(N-methylcarbamoyloxy)-TC-dec-8-en-3-one (120–122)
24. 4-oxa-1-methyl-5-(N-methoxymethylcarbamoyloxy)-TC-dec-8-en-3-one (125–127).

EXAMPLE 25

4-oxa-5-(N-methylcarbamoyloxy)-tricyclo-[5,2,1,0$^{2,6}$]dec.8-en-3-one

A solution of 33.2 g of 4-oxa-5-hydroxytricyclo[5,2,1,0$^{2,6}$]dec-8-en-3-one in 50 ml of tetrahydrofuran has 12.5 g of methyl isocyanate and 170 mg of tin(II) octanoate added to it at room temperature. The slightly exothermic reaction is over within 90 minutes. The pasty reaction product is diluted with 30 ml of ether and cooled to 2°C. The crystalline product is suction filtered. The yield is 38.5 g and the melting point is 163° to 165°C,

EXAMPLES 26 TO 35

The following carbamates are synthesized analogously to Example 25. Melting points in °C are given in parenthesis. TCD = tricyclo[5,2,1,0$^{2,6}$]dec-8-en-3-one.

26. 4-oxa-5-(N-n-propylcarbamoyloxy)-TCD (81–83)
27. 4-oxa-5-(N-sec.-butylcarbamoyloxy)-TCD (105–108)
28. 4-oxa-5-(N-cyclopentylcarbamoyloxy)-TCD (132–133)
29. 4-oxa-5-(N-cyclohexylcarbamoyloxy)-TCD (164–167)
30. 4-oxa-5-(N-(1'-methylthioprop-2'-yl)-carbamoyloxy)-TCD (108–110)
31. 4-oxa-5-(N-pent-1'-yn-3'-yl)-carbamoyloxy)-TCD (142–145)
32. 4-oxa-5-(N-(3'-chloromethylprop-3'-yl)-carbamoyloxy)-TCD (99–101)
33. 4-oxa-5-(N-β-methylthidethylcarbamoyloxy)-TCD (122–124)
34. 4-oxa-5-(N-β-ethylthioethylcarbamoyloxy)-TCD (105–107)
35. 4-oxa-5-(N-β-chloroethylcarbamoyloxy)-TCD (106–108).

EXAMPLE 36

4-oxa-5-(N-methylcarbamoyloxy)-tricyclo[5,2,1,0$^{2,6}$]-decan-3-one 33.5 g of 4-oxa-5-(N-methylcarbamoyloxy)-tricyclo[5,2,1,0$^{2,6}$]dec-8-en-3-one is hydrogenated in 170 ml of tetrahydrofuran in contact with an Ni/SiO$_2$ catalyst (25% nickel) at 60°C and a hydrogen pressure of 170 atmospheres gauge. The catalyst is separated. The solvent is removed in vacuo. The residue is recrystallized from a mixture of ethyl acetate and hexane with an addition of activated carbon. The yield is 18.1 g and the melting point is 144° to 146°C.

Elementary analysis (C$_{11}$H$_{15}$NO$_4$). Calculated: C, 58.7; H, 6.7; N, 6.2; O, 28.4.

Found: C, 59.2; H, 6.9; N, 6.3; O, 28.1.

EXAMPLE 37

12 g of 4-oxa-5-(N-benzylcarbamoyloxy)-tricyclo-[5,2,1,0$^{2,6}$]dec-8-en-3-one is hydrogenated as described in Example 36 and 11.8 g of 4-oxa-5-(N-benzylcarbamoyloxy)-tricyclo[5,2,1,0$^{2,6}$]decan-3-one is obtained which has a melting point of 123° to 126°C.

EXAMPLE 38

14.5 g of 4-oxa-5-(N-phenylcarbamoyloxy)-tricyclo[5,2,1,0$^{2,6}$]-dec-8-en-3-one is hydrogenated in 80 ml of tetrahydrofuran at 60°C and 170 atmospheres gauge hydrogen pressure as described in Example 36. 12.2 g of 4-oxa-5-(N-phenylcarbamoyloxy)-tricyclo[5,2,1,0$^{2,6}$]-decan-3-one is obtained having melting point of 167° to 168°C.

EXAMPLE 39

83 g of 4-oxa-5-hydroxytricyclo[5,2,1,0$^{2,6}$]dec-8-en-3-one is added within 15 minutes to 145 g of methyl isocyanate at a temperature of 30° to 38°C. The added γ-hydroxylactone added thus passes into solution with an exothermic reaction. When the reaction is over, crystals separate out and these are suction filtered and recrystallized from acetone. The yield is 52.2 g of 4-oxa-5(N-methylcarbamoyloxy)-tricyclo[[5,2,1,0$^{2,6}$]-dec-8-en-3-one having a melting point of 159° to 161°C.

EXAMPLE 40

A mixture of 16.7 g of cyclopentadiene and 5 ml of ethyl acetate is added to a solution of 40.6 g of 2-(N-phenylcarbamoyloxy)-2,5-dihydrofuran-5-one in 150 ml of ethyl acetate at a temperature of 40°C and the whole is left for 2½ hours at this temperature. The solvent is distilled off. A crystalline residue remains which after it has been recrystallized from ethyl acetate melts at 172° to 175°C. 36 g of 4-oxa-5-(N-phenylcarbamoyloxy)-tricyclo[5,2,1,0$^{2,6}$]dec-8-en-3-one is obtained.

EXAMPLE 41

A solution of 5.2 g of 2-(N-methylcarbamoyloxy)-2,5-dihydrofuran-5-one in 14 ml of tetrahydrofuran has a mixture of 4.4 g of cyclopentadiene and 4 ml of tetrahydrofuran added to it at room temperature and then the whole is left at room temperature for 16 hours and cooled to 0°C. The crystals which have been deposited are suction filtered. The yield is 6.1 of the melting point 163° to 164°C. This is 4-oxa-4-(5-methylcarbamoyloxy)-tricyclo[5,2,1,0$^{2,5}$]dec-8-en-3-one.

EXAMPLE 42

24 g of cyclohexadiene-1,3 and 100 mg of hydroquinone are added to a solution of 21 g of 2-(N-methylcarbamoyloxy)-2,5-dihydrofuran-5-one in 40 ml of tetrahydrofuran and the whole is heated for 6 hours at 120°C in an autoclave having a capacity of 500 ml. The reaction product is treated with activated carbon, the solution is concentrated and the residue is crystallized from ethyl acetate. 8.7 g of 4-oxa-(N-methylcarbamoyloxy)-tricyclo[5,2,2,2,0$^{2,6}$]-undec-8-en-3-one of the melting point 146° to 148°C is obtained.

EXAMPLE 43

2.64 g of cyclopentadiene is added to a solution of 1.43 g of 2-carbamoyloxy-2,5-dihydrofuran-5-one (prepared by the reaction of malealdehyde pseudoacid with chlorosulfonyl isocyanate followed by hydrolysis) in 40 ml of ethyl acetate at 40°C and the whole is heated for 3 hours at 60°C and then cooled to 0°C. The crystals which have been deposited are suction filtered. The yield is 1.3 g of 4-oxa-5-(carbamoyloxy)-tricyclo[5,2,1,0$^{2,6}$]dec-8-en-3-one having a melting point of 179° to 182°C.

EXAMPLE 44

24 g of cyclohexadiene and 100 mg of hydroquinone are added to a solution of 1.43 g of 2-carbamoyloxy-2,5-dihydrofuran-5-one in 80 ml of tetrahydrofuran and the whole is heated for 6 hours at 130°C (in an autoclave having a capacity of 500 ml). The reaction product is filtered and the solution is concentrated. 6.3 g of 4-oxa-5-(carbamoyloxy)-tricyclo[5,2,2,0$^{2,6}$]undec-8-en-3-one having a melting point of 186°C crystallizes out.

The compounds set out in Examples 1 to 35 are obtained in a corresponding manner by a Diels-Alder reaction with comparable yields.

EXAMPLE FOR TABLETS

| | |
|---|---|
| 1. 4-oxa-5-(N-methylcarbamoyloxy)-tricyclo-[5,2,1,0$^{2,6}$]dec-8-en-3-one | 30 mg |
| 2. polyvinylpyrrolidone (mean molecular weight 25,000) | 20 mg |
| 3. polyethylene glycol (mean molecular weight 4,000) | 14 mg |
| 4. hydroxypropylmethylcellulose | 40 mg |
| 5. talc | 4 mg |
| 6. magnesium stearate | 2 mg |
| | 110 mg |

The active ingredient is moistened with polyvinylpyrrolidone in 10% aqueous solution, forced through a sieve having an internal mesh width of 1.0 mm and dried at 50°C. The granules are mixed with polyethylene glycol (mean molecular weight 4,000), hydroxypropylmethylcellulose, talc and magnesium stearate and pressed into tablets of 110 mg.

EXAMPLE FOR DRAGEES

| | |
|---|---|
| 1. 4-oxa-5-(carbamoyloxy)-tricyclo [5,2,1,0$^{2,6}$]dec-8-en-3-one | 60 mg |
| 2. lactose | 80 mg |
| 3. maize starch | 30 mg |
| 4. polyvinylpyrrolidone | 4 mg |
| 5. magnesium stearate | 1 mg |
| | 175 mg |

A mixture of the active ingredient with lactose and maize starch is granulated with an 8% aqueous solution of the polyvinylpyrrolidone through a sieve 1.5 mm, dried at 50°C and again rubbed through a sieve at 1.0 mm. The granules obtained are mixed with magnesium stearate and pressed to dragee cores. The dragee cores obtained are provided in the conventional way with a coating consisting essentially of sugar and talc.

EXAMPLE FOR GELATIN CAPSULES

A gelatin capsule contains:

| | |
|---|---|
| 1. 4-oxa-5-(N-methylcarbamoyloxy)-tricyclo-[5,2,2,0$^{2,6}$]undec-8-en-3-one | 80.0 mg |
| 2. maize starch | 210.0 mg |
| 3. silicone dioxide (AEROSIL) | 6.0 mg |
| 4. magnesium stearate | 4.0 mg |
| | 300.0 mg |

The substances are mixed intensely and filled into gelatin capsules.

EXAMPLE FOR SUPPOSITORIES

One cone contains:

| | |
|---|---|
| 1. 4-oxa-5-(N-methylcarbamoyloxy)-tricyclo-[5,2,1,0$^{2,6}$]dec-8-en-3-one | 100.0 mg |
| 2. Suppository substance, for example Adeps neutralis (STADIMOL) | 1650.0 mg |
| | 1750.0 mg |

The finely powdered active ingredient is stirred by means of an immersion homogenizer into the melted suppository substance which has been cooled to 40°C. The product is poured at 38°C into slightly precooled molds.

We claim:
1. A compound of the formula (I):

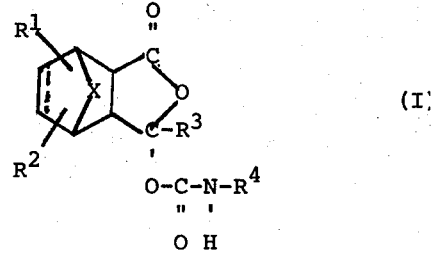

in which

The dotted line denotes a double bond which may be hydrogenated;

X is —$(CH_2)_n$— in which $n$ is one of the integers from 1 to 2, $R^1$ is hydrogen or alkyl of one to four carbon atoms, $R^2$ is hydrogen, $R^3$ is hydrogen, and $R^4$ is hydrogen or a linear or branched, saturated or unsaturated alkyl of one to four carbon atoms which may bear a substituent selected from the group consisting of chlorine, alkoxy of one to four carbon atoms, dialkylamino of one to four carbon atoms in the alkyl, cycloalkyleneimino of five to seven ring members and phenyl.

2. 4-oxa-5-(N-methylcarbamoyloxy)-tricyclo[5,2,1,0$^{2,6}$]dec-8-en-3-one.

3. 4-oxa-5-(carbamoyloxy)-tricyclo[5,2,1,0$^{2,6}$]dec-8-en-3-one.

4. 4-oxa-5-(N-methylcarbamoyloxy)-tricyclo[5,2,2,0$^{2,6}$]undec-8-en-3-one.

* * * * *

UNITED STATES PATENT AND TRADEMARK OFFICE
CERTIFICATE OF CORRECTION

PATENT NO. : 3,965,119
DATED : June 22, 1976
INVENTOR(S) : AMANN et al

It is certified that error appears in the above-identified patent and that said Letters Patent are hereby corrected as shown below:

In Column 7, Line 36, delete "dextropropoxypitene" and substitute -- dextropropoxyphene --

In Column 7, Line 46, delete " ... i.e. that does ..." and substitute -- ... i.e. that dose ... --

In Column 11 Line 22, delete " ... is 6.1 of ... " and substitute -- ... is 6.1g of ... --

Signed and Sealed this

Fifth Day of April 1977

[SEAL]

Attest:

RUTH C. MASON
*Attesting Officer*

C. MARSHALL DANN
*Commissioner of Patents and Trademarks*